United States Patent [19]
Rubin et al.

[11] Patent Number: 5,821,223
[45] Date of Patent: Oct. 13, 1998

[54] METHOD OF STIMULATING CELL GROWTH WITH A NOVEL BROAD SPECTRUM HUMAN LUNG FIBROBLAST-DERIVED MITOGEN

[75] Inventors: Jeffrey S. Rubin, Rockville; Andrew M.-L. Chan, Bethesda, both of Md.; Stuart A. Aaronson, Great Falls, Va.

[73] Assignee: The United States of America as represented by the Department of Health and Human Services, Washington, D.C.

[21] Appl. No.: 238,742

[22] Filed: May 5, 1994

Related U.S. Application Data

[62] Division of Ser. No. 582,063, Sep. 14, 1990, abandoned.

[51] Int. Cl.⁶ .......................... A61K 38/18; C07K 14/475
[52] U.S. Cl. .................................. 514/12; 514/2; 530/399
[58] Field of Search .......................... 514/2, 12; 530/350, 530/399, 351; 435/240.1, 240.2, 325; 424/85.2

[56] References Cited

U.S. PATENT DOCUMENTS

| 5,004,805 | 4/1991 | Gohda et al. . | |
|---|---|---|---|
| 5,342,831 | 8/1994 | Nakamura et al. | 514/12 |
| 5,362,716 | 11/1994 | Kmiecik et al. | 514/12 |

FOREIGN PATENT DOCUMENTS 0 246 753   11/1987   European Pat. Off. .

OTHER PUBLICATIONS

T. Nakamura et al., "Molecular Cloning and Expression of Human Hepatocyte Growth Factor", *Nature* 342: 440–443 (1989).

K. Miyazawa et al., "Molecular Cloning and Sequence Analysis of cDNA For Human Hepatocyte Growth Factor", *Biochem. and Biophys. Res. Comm.* 163(2): 967–973 (1989).

Gohda, et al., "Purification and Partial Characterization of Hepatocyte Growth Factor from Plasma of a Patient with Fulminant Hepatic Failure", A.S.C.I., Feb. 1988, pp. 414–419.

Zarnegar, et al., "Purification and Biological Characterization of Human Hepatopoietin A, a Polypeptide Growth Factor for Hepatocytes", Cancer Research 49, Jun. 15, 1989, pp. 3314–3320.

Gherardi, et al., "Purification of Scatter Factor, a Fibroblast–Derived Basic Protein that Modulates Epithelial Interactions and Movement", Proc. Natl. Acad. Sci. USA, vol. 86, 1989, pp. 5844–5848.

Nakamura, et al., "Purification and Subunit Structure of Hepatocyte Growth Factor from Rat Platelets", Febs Letters, vol. 224, No. 2, 1987, pp. 311–316.

*Primary Examiner*—Marianne P. Allen
*Attorney, Agent, or Firm*—Needle & Rosenberg, P.C.

[57] ABSTRACT

The present invention relates to a potent mitogenic growth factor called plasminogen-like growth factor (PLGF) isolated from conditioned medium of human lung fibroblasts. The protein has an apparent molecular weight under reducing conditions of 87 kDa and is structurally related to hepatocyte growth factor (HGF); however unlike HGF, which was reported to be specific for hepatic cells, PLGF stimulates a wide spectrum of target cells including melanocytes, endothelial cells and epithelial cells but excludes fibroblast cells.

The present invention further relates to recombinant cloned DNA fragments and expression cell systems expressing biologically active PLGF. The availability of purified PLGF as well as immunological and molecular probes should facilitate the study of proliferative disorders in which the factor plays an important role.

10 Claims, 12 Drawing Sheets

```
         10        20        30        40        50        60        70        80        90       100
MMVV TKLLPALLLQHVLLHLLLLPIAIPYAEQ QRKRRNT IHEFKKSAKT T LIK IDPALK IKTKKVVNTADQCANRCTRNKGLPF TCKAF VF DKARKQCLWF P
                                                 HK                                    N

FNSMSSGVKKEFGHEFDLYENKDYIRNCIIGKGRSYKGTVSITKSGIKCQPWSSMIPHEHSYRGKDLQENYCRNPRGEEGGPWCFTSNPEVRYEVCDIPQ       200
                                                         FLPSS

CSEVECMTCNGESYRGCLMDHTESGKICQRWDHQTPHRHKFLPERYPDKGFDDNYCRNPDGQPPPWCYTLDPHTRWEYCAIKTCADNTMNDTDVPLETTEC       300
                                                                                              V  M

IQCQGEGYRGTVNTIWNGIPCQRWDSQYPHEHDMTPENFKCKDLRENYCRNPDGSESPWVCFTTDPNIRVGYCSQIPNCDMSHGQDCYRGNGKNYMCNLSQ      400
                  A     K                                                           N

TRSGLTCSMWDKNMEDLHRHIFWEPDASKLNENYCRNPDDDAHGPWCYTGNPLIPWDYCPISRCEGDTTPTIVNLDHPVISCAKTKQLRVVNGIPTRTNI      500
    N                                                                                             V

GMWVSLRYRNKHICGGSLIKESWVLTARQCFPSRDLKDYEAWLGIHDVHGRGDEKCKQVLNVSQLVYGPEGSDLVLMKLARPAVLDDFVSTIDLPNYGCT       600
     I                                         E  R                                    N

IPEKTSCSVYGWGYTGLINYDGLLRVAHLYIMGNEKCSQHHRGKVTLNESEICAGAEKIGSGPCEGDYGGPLVCEQHKMRMVLGVIVPGRGCAIPNRPGI        700

FVRVAYYAKWIHKIILTYKVPQS
```

PLGF FROM 1 TO 2172

```
        10         20         30         40         50         60         70
atgtgggtga ccaaactcct gccagccctg ctgctgcagc atgtccctcct gcatctcctc ctgctccca
        80         90        100        110        120        130        140
tcgccatccc ctatgcagag ggacaaagga aaagaagaaa tacaattcat gaattcaaaa aatcagcaaa
       150        160        170        180        190        200        210
gactacccta atcaaaatag atccagcact gaagataaaa accaaaaaag tgaatactgc agaccaatgt
       220        230        240        250        260        270        280
gctaatagat gtactaggaa taaaggactt ccattcactt gcaaggcttt tgttttgat aaagcaagaa
       290        300        310        320        330        340        350
aacaatgcct ctggttcccc ttcaatagca tgtcaagtgg agtgaaaaaa gaatttggcc atgaatttga
       360        370        380        390        400        410        420
cctctatgaa acaaaagact acattagaaa ctgcatcatt ggtaaaggac gcagctacaa gggaacagta
       430        440        450        460        470        480        490
tctatcacta agagtggcat caaatgtcag ccctggagtt ccatgatacc acacgaacac agctatcggg
       500        510        520        530        540        550        560
gtaaagacct acaggaaaac tactgtcgaa atactcgagg ggaagaaggg ggaccctggt gtttcacaag
```

FIG. 6A

```
570        580        590        600        610        620        630
caatccagag gtacgctacg aagtctgtga cattcctcag tgttcagaag ttgaatgcat gacctgcaat 640        650        660        670        680        690        700
ggggagagtt atcgaggtct catggatcat acagaatcag gcaagatttg tcagcgctgg gatcatcaga 710        720        730        740        750        760        770
caccacaccg gcacaaattc ttgcctgaaa gatatcccga caagggcttt gatgataatt attgccgcaa 780        790        800        810        820        830        840
tcccgatggc cagccgaggc catggtgcta tactccttgac cctcacaccc gctgggagta ctgtgcaatt 850        860        870        880        890        900        910
aaaacatgcg ctgacaatgac tatgaatgac actgatgttc ctttgaaaac aactgaatgc atccaaggtc 920        930        940        950        960        970        980
aaggagaagg ctacagggggc actgtcaata ccatttggaa tggaattcca tgtcagcgtt gggattctca 990        1000       1010       1020       1030       1040       1050
gtatcctcac gagcatgaca tgactcctga aaatttcaag tgcaaggacc tacgagaaaa ttactgccga 1060       1070       1080       1090       1100       1110       1120
aatccagatg ggtctgaatc acctggtgt tttaccactg atccaaacat ccgagttggc tactgctccc
```

FIG. 6B

```
1130       1140       1150       1160       1170       1180       1190
aaattccaaa ctgtgatatg tcacatggac aagattgtta tcgtgggaat ggcaaaaatt atatgggcaa 1200       1210       1220       1230       1240       1250       1260
cttatcccaa acaagatctg gactaacatg ttcaatgtgg gacaagaaca tggaagactt acatcgtcat 1270       1280       1290       1300       1310       1320       1330
atcttctggg aaccagatgc aagtaagctg aatgagaatt actgccgaaa tccagatgat gatgctcatg 1340       1350       1360       1370       1380       1390       1400
gaccctggtg ctacacggga aatccactca ttcccttgga ttattgccct atttctcgtt gtgaaggtga 1410       1420       1430       1440       1450       1460       1470
taccacacct acaatagtca atttagacca tcccgtaata tcttgtgcca aaacgaaaca attgcgagtt 1480       1490       1500       1510       1520       1530       1540
gtaaatggga ttccaacacg aacaaacata ggatggatgg ttagtttgag atacagaaat aaacatatct 1550       1560       1570       1580       1590       1600       1610
gcggaggatc attgataaag gagagttggg ttcttactgc acgacagtgt ttcccttctc gagacttgaa 1620       1630       1640       1650       1660       1670       1680
agattatgaa gcttggcttg gaattcatga tgtccacgga agagagatg  agaaatgcaa acaggttctc
```

FIG. 6C

```
      1690       1700       1710       1720       1730       1740       1750
aatgtttccc agctggtata tggccctgaa ggatcagatc tggttttaat gaagcttgcc aggcctgctg 1760       1770       1780       1790       1800       1810       1820
tcctggatga ttttgttagt acgattgatt tacctaatta tggatgcaca attcctgaaa agaccagttg 1830       1840       1850       1860       1870       1880       1890
cagtgtttat ggctggggct acactggatt gatcaactat gatggcctat tacgagtggc acatctctat 1900       1910       1920       1930       1940       1950       1960
ataatgggaa atgagaaatg cagccagcat catcgaggga aggtgactct gaatgagtct gaaatatgtg 1970       1980       1990       2000       2010       2020       2030
ctggggctga aaagattgga tcaggaccat gtgaggggga ttatggtggc ccacttgttt gtgagcaaca 2040       2050       2060       2070       2080       2090       2100
taaaatgaga atggttcttg gtgtcattgt tcctggtcgt ggatgtgcca ttccaaatcg tcctggtatt 2110       2120       2130       2140       2150       2160       2170
tttgtccgag tagcatatta tgcaaaatgg atacacaaaa ttattttaac atataaggta ccacagtcat ag
```

FIG. 6D

METHOD OF STIMULATING CELL GROWTH WITH A NOVEL BROAD SPECTRUM HUMAN LUNG FIBROBLAST-DERIVED MITOGEN

This application is a divisional of U.S. Ser. No. 07/582,063, filed Sep. 14, 1990 now abandoned.

BACKGROUND OF THE INVENTION

1. Field of the Invention

The present invention identifies a new fibroblast-derived mitogen called plasminogen-like growth factor (PLGF) with activity on melanocytes, epithelial and endothelial cells. In particular, the present invention relates to the purification, molecular cloning and recombinant expression of PLGF which bears strong sequence homology to HGF but yet exhibits broad target cell specificity whose pattern is distinct from HGF and any other known growth factor.

2. Background of the Invention

Growth factors are widely believed to play important roles in normal development and wound healing. (R. James and R. A. Bradshaw, Annu. Rev. Biochem. 53, 259 (1984); T. F. Deuel, Annu. Rev. Cell Biol. 3, 443 (1987); A. Barbul, E. Pines, M. Caldwell, T. K. Hunt, Eds., Growth Factors and Other Aspects of Wound Healing: Biological and Clinical Implications. Progress in Clinical and Biological Research Vol 266 (Alan R. Liss, New York, 1988)). Their abnormal expression has been implicated in neoplasia as well as a variety of other proliferative disorders. (M. B. Sporn and E. D. Harris, Jr., AM. J. Med. 70, 1231 (1981); A. S. Goustin, E. B. Leof, G. D. Shipley, H. L. Moses, Cancer Res. 46, 1015 (1986); M. B. Sporn, A. B. Roberts, J. Clin. Invest. 78, 329 (1986); R. Ross, New Engl. J. Med. 314, 488 (1986). Accumulating evidence indicates that mesenchymal interactions presumably mediated diffusible substances had a major impact on epithelial cell proliferation (G. R. Cunha, L. W. K. Chung, J. M. Shannon, 0. Taguchi & H. Fujii, Recent Prog. Hormone Res. 39, 559 (1983); R. H. Sawyer and J. F. Fallow, Eds., Epithelial Mesenchymal Interaction During Development (Praeger New York, 1983); S. L. Schor, A. M. Howell & D. Crowther, Exp. Cell Biol. 55, 11 (1987), yet there is relatively little knowledge of such stromal cell effectors. Systematic efforts to isolate and characterize epithelial-acting mitogens produced by stromal cells have led to the discovery of keratinocyte growth factor (KGF), a new member of the FGF family, specific for epithelial cells. (J. S. Rubin, H. Finch, P. W. Taylor, W. G. Rudikoff & S. A. Aaronson, Proc. Natl. Acad. Sci. U.S.A. 86, 802–806 (1989); P. W. Finch et al., Science 245, 752 (1989).

It is clear that a need exists for identifying new epithelial cell mitogenic activities produced by stromal fibroblasts. The present invention describes the purification and molecular cloning of a new growth factor called PLGF derived from stromal fibroblasts possessing a novel spectrum of target cells and its unexpected homology to other proteins involved in growth and tissue remodeling.

SUMMARY OF THE INVENTION

It is an object of the present invention to provide a biologically active growth factor called plasminogen-like growth factor (PLGF) having cell specificity for melanocytes, endothelial cells and epithelial cells and methods of treating wounds and tissue regeneration therewith.

Various other objects and advantages of the present invention will become obvious from the drawings and the following description of the invention.

In one embodiment, the present invention relates to plasminogen-like growth factor (PLGF) protein that is substantially free of proteins with which PLGF is normally associated and antibodies specific therefor.

In another embodiment, the present invention relates to a DNA segment encoding PLGF protein.

In yet another embodiment, the present invention relates to a DNA segment encoding the PLGF protein and recombinant constructs comprising the same.

In a further embodiment, the present invention relates to a host cell comprising the above described DNA construct.

Another embodiment of the present invention relates to a process of making PLGF. The method comprises culturing host cells described above under conditions such that the DNA segment encoding PLGF is expressed and produced, and isolating the PLGF protein.

In a further embodiment, the present invention relates to methods of inhibiting cell proliferation comprising administering a therapeutic amount of antibody specific for PLGF protein to an animal.

In yet another embodiment, the present invention relates to a method of stimulating the growth of cells in which PLGF is contacted to cells under conditions such that stimulation of cell growth is effected.

BRIEF DESCRIPTION OF THE DRAWINGS

FIG. 1 shows a NaDodSO$_4$/PAGE analysis of the active pool from reverse-phase c$_4$ HPLC. Approximately 0.4 µg of purified protein was redissolved in sample buffer either lacking (−) or containing (+) 2.5% 2-mercaptoethanol as reducing agent, boiled for 3 min and electrophoresed in a 10% polyacrylamide SDS gel which was subsequently silver-strained. The bands associated with mitogenic activity are indicated by arrows.

FIG. 2 shows the mitogenic activity of the C4-purified growth factor on B5/589 human mammary epithelial cells. Incorporation of [3H]thymidine into trichloroacetic acid-insoluble DNA was determined as previously described. (Rubin et al., 1989). Protein concentration was estimated by optical density, assuming A 1%/214=140. Each data point was the mean of duplicate measurements which varied<5000 cpm.

FIG. 3 demonstrates tyrosine phosphorylation in response to the newly isolated growth factor. After exposure of B5/589 cells to HSAC-purified growth factor (100 ng/ml) for varying intervals at 37° C., 1.5 mg protein from each cell lysate was immunoprecipitated with phosphotyrosine antiserum, electrophoresed in an 8% polyacrylamide-NaDodSO$_4$, gel and immunoblotted with phosphotyrosine antiserum (D. P. Bottaro, J. S. Rubin, D. Ron, P. W. Finch, C. Florio, & S. A. Aaronson, J. Biol. Chem. Vol. 265 pp. 12767–12770, (1990). Antiserum preincubated with 2 mM phenyl phosphate as competitor was utilized as a control (lane 5). The major band seen in response to the growth factor, pp. 145, is indicated by an arrow.

FIG. 4 (A) Schematic presentation of cDNA clones encoding the mitogen. The largest cDNA insert, λ9, and representative ~3 kb inserts, λ1a and λ22 are shown above a diagram of the complete coding sequence and the adjacent 5' and 3' untranslated regions. The coding sequence is boxed; untranslated regions are represented by a line. The restriction enzymes are: X, Xho I; Rv, Eco Rv; K, Kpn I. An expanded view of the coding sequence reveals the major domains and the amino acid residues defining their borders: SIG, signal peptide; N-TERM; K1, K2, K3 and K4 are kringles [an 80 amino acid motif containing three disulfide bridges also found in plasminogen, prothrombin, coagulation factor XII, tissue plasminogen activator, urokinase and apolipoprotein (a) (L. Sottrup-Jensen, H. Claeys, M. Zajdel, T. E. Peterson & S. Magnusson in Progress in Chemical Fibrinolysis and Thrombolysis, J. F. Davidson, M. M. Samama, and P. C. Desnoyers, Eds., (Raven, N.Y.), vol. 3, pp. 191–209, (1978); B. Furie & B. C. Furie, Cell 53, 505–518 (1988); J. W. McLean, J. E. Tomlinson, W.-J. Kuang, D. L. Eaton, E. Y. Chen, G. M. Fless, A. N. Scanu & R. M. Lawn Nature 330, 132–137 (1987); L, linker ending at internal cleavage site; PROTEASE-LIKE, corresponding to serine protease domain. The arrowhead indicates the site of the 5 amino acid deletion relative to the published HGF sequences.

(B) Identification of the growth factor mRNAs by RNA blot analysis. An RNA blot of M426 total cellular RNA was hybridized with a [$^{32}$P]-labeled 2.2-Kb fragment of λ1a containing the entire coding sequence [nucleotides (−27) to 2199] according to standard procedures.

(C) Predicted growth factor amino acid sequence. Amino acids are designated by the standard single letter code. The experimentally determined peptide sequence obtained from the purified growth factor is underlined. The putative signal peptide is shaded. The 5 amino acid segment absent from our sequence compared to both reported HGF sequences (K. Miyazawa, H. Tsubouchi, D. Naka, K. Takahashi, M. Okigaki, N. Arakai, H. Nakayama, S. Hirono, O. Sakiyama, E. Gohda, Y. Daikuhara & N. Kitamura, Biochem. Biophys. Res. Comm. 163, 967–973 (1989); Nakamura T. et al. Nature 342, 440–443) (1989) is shown in a box below the deletion site. The additional differences in the HGF sequence reported by Nakamura et al. (Nakamura T. et al. 1989)) are noted below our sequence. Highlighted among these differences are a boxed C—>R substitution and an overlined RGD segment. The internal cleavage site, conserved relative to plasminogen (Sottrup-Jensen et al., 1978) in Progress in Chemical Fibrinolysis and Thrombolysis; Davidson, J. F., Samama, M. M. and Desnoyers, P. C., Eds. (Raven, N.Y.), Vol. 3, pp. 191–209; Robbins et al., J. Biol. Chem. 242, 2333–2342, (1967), is identified by an open arrowhead; the substitutions for catalytically active residues are marked with asterisks.

FIG. 5 (A) Mitogenic activity of the recombinant factor on B5/589 cells. Conditioned medium from COS-1 cells transfected with the λ1a coding sequence in the sense (O) or antisense (Δ) orientation was collected, filtered, and assayed on B5/589 cells for stimulation of [3H]thymidine incorporation. The medium from cells transfected with the coding sequence in the sense orientation was also tested in the presence of an antiserum (final dilution 1/50) which specifically neutralized the activity of the purified growth factor (●).

Each data point was the mean of duplicate measurements which varied <3500 cpm.

(B) Biosynthesis of the growth factor in M426 and transfected COS cells. Proteins labeled with $^{35}$S-methionine from cell lysates (CL) or conditioned medium (CM) were immunoprecipitated with nonimmune serum (N) or neutralizing antiserum prepared against the purified growth factor (I), electrophoresed under reducing conditions in a 10% polyacrylamide-NaDodSO$_4$ gel and detected by autoradiography. COS-S and COS-AS refer to cells transfected with cDNA in the sense or antisense orientation, respectively. FIG. 6 shows the nucleotide sequence of the PLGF coding region from cDNA insert λ1A; numbering begins with the initiation codon.

DETAILED DESCRIPTION OF THE PREFERRED EMBODIMENTS

The present invention relates, in part, to a new stromal cell mediator of epithelial cell proliferation and its encoding DNA. One embodiment of the present invention relates to a new substantially pure form of a biologically active fibroblast derived growth factor called plasminogen-like growth factor (PLGF) with a broad spectrum of mitogenic cell specificity that includes melanocytes, endothelial cells and epithelial cells but excludes fibroblasts. Substantially pure as used herein refers to a preparation in which the growth factor is both the most abundant entity and free of greater than 99.9% of the proteins which are normally present in its milieu.

PLGF can be isolated from conditioned medium of human embryonic lung fibroblasts, substantially free from other proteins. Following the instructions presented herein, an active form of the growth factor of the present invention can be obtained by one skilled in the art using standard methodologies for protein purification without undue experimentation. The protein is naturally synthesized as a single chain form having a molecular weight of 87 kDa and a portion of it is subsequently processed to yield a disulfide-linked heterodimer containing 55–60 kDa and 32–34 kDa chains as determined by SDS-PAGE under non-reducing and reducing conditions.

As depicted in Table I, PLGF exhibits a broad target cell specificity whose pattern is distinct from known growth mediators. Unlike KGF, previously described growth factor of stromal cell origin that exhibits tightly restricted epithelial cell target specificity, PLGF exhibits potent mitogenic activity for melanocytes and endothelial cells in addition to epithelial cells. PLGF is also expressed in cultured stromal cells derived from skin, gastrointestinal tract, prostate as well as lung. Because the endothelial and epithelial cells all reside in close approximation to these stromal fibroblasts, it is suggested that the factor acts as a paracrine mediator of normal proliferation for a wide spectrum of cell types. Accordingly, the present invention also relates to applications of PLGF in wound healing and tissue remodeling and regeneration. In particular, the growth factor may be used to heal damaged gastrointestinal or respiratory, or other epithelial tissues, or promote angiogenesis. Furthermore, the growth may prove useful as a melanocyte stimulating factor in pigmentation diseases such as vitiligo.

Figure 4A:
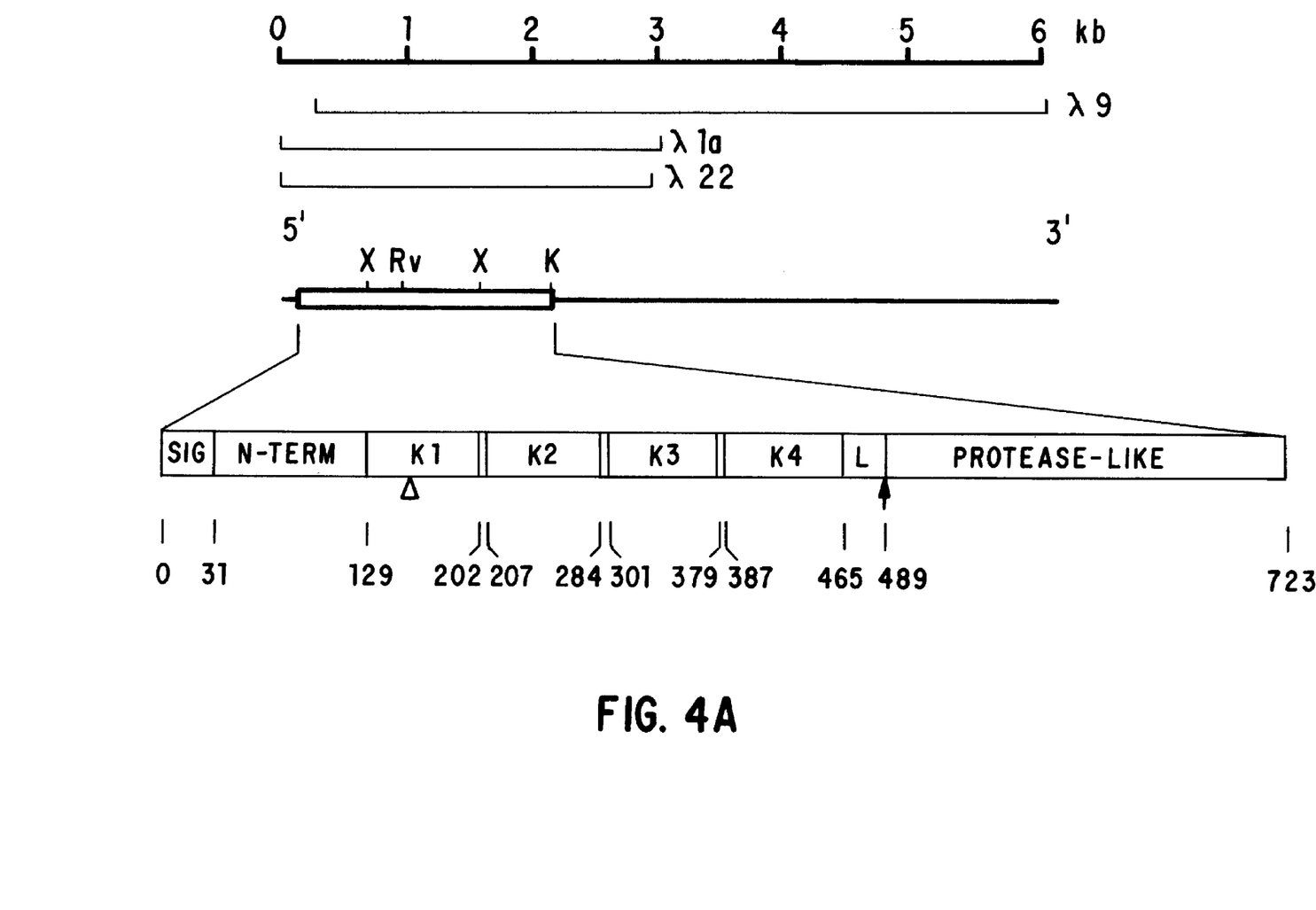

The present invention also relates to DNA fragments encoding PLGF, or allelic or species variations thereof. One embodiment of this aspect of an invention relates to the 3.0 kb fragment obtained from a DNA library of M426 human embryonic lung fibroblasts. The fragment, called λ spans the entire coding region of PLGF and contains a 2172 nucleotide open reading frame encoding the protein. Other 3 kb DNA fragments and a 6 kb DNA fragment obtained from the M426 library that encode PLGF are also embodied in the invention. This is schematically presented in FIG. 4 (A) wherein the DNA fragments are compared to each other and to PLGF (See example 3 below). The predicted protein sequence of PLGF obtained from λ DNA fragment reveals a complete identity to known HGF except for a unique absence of a 5 amino acid stretch corresponding to a 15 base pair deletion in PLGF (See FIG. 4C and Example 3 below). Further differences found between PLGF and HGF sequences are 14 other single amino acid substitutions scattered throughout the molecule.

The present invention further relates to recombinant DNA molecules and to host cells transformed therewith. Using standard methodology well known in the art, a recombinant DNA molecule comprising a vector and a DNA fragment encoding the PLGF protein of this invention can be constructed without undue experimentation. The DNA fragment can be isolated from human embryonic lung fibroblasts or it can take the form of a cDNA clone produced using methods well known to those skilled in the art. By employing these standard techniques, we have been able to obtain biologically active PLGF with the pcDV vector in COS-1 cells as well as stable expression with the vectors in NIH/3T3 and B5/589 cells. Possible vectors include the ones just mentioned in addition to others suitable for prokaryotic, baccu-lovirus or other expression systems.

The present invention further relates to antibodies which exhibit neutralization of the mitogenic activity of PLGF. One skilled in the art using standard methodology described in the prior art and in example 4 described below can raise polyclonal antibodies and monoclonal antibodies to PLGF, or allelic or species variation thereto, which antibodies can be used to block the mitogenic activity of PLGF. These or other similar antibodies also could be used to identify the growth factor by means of immunoblot analysis or radioimmuno-precipitation.

Figure 5A:
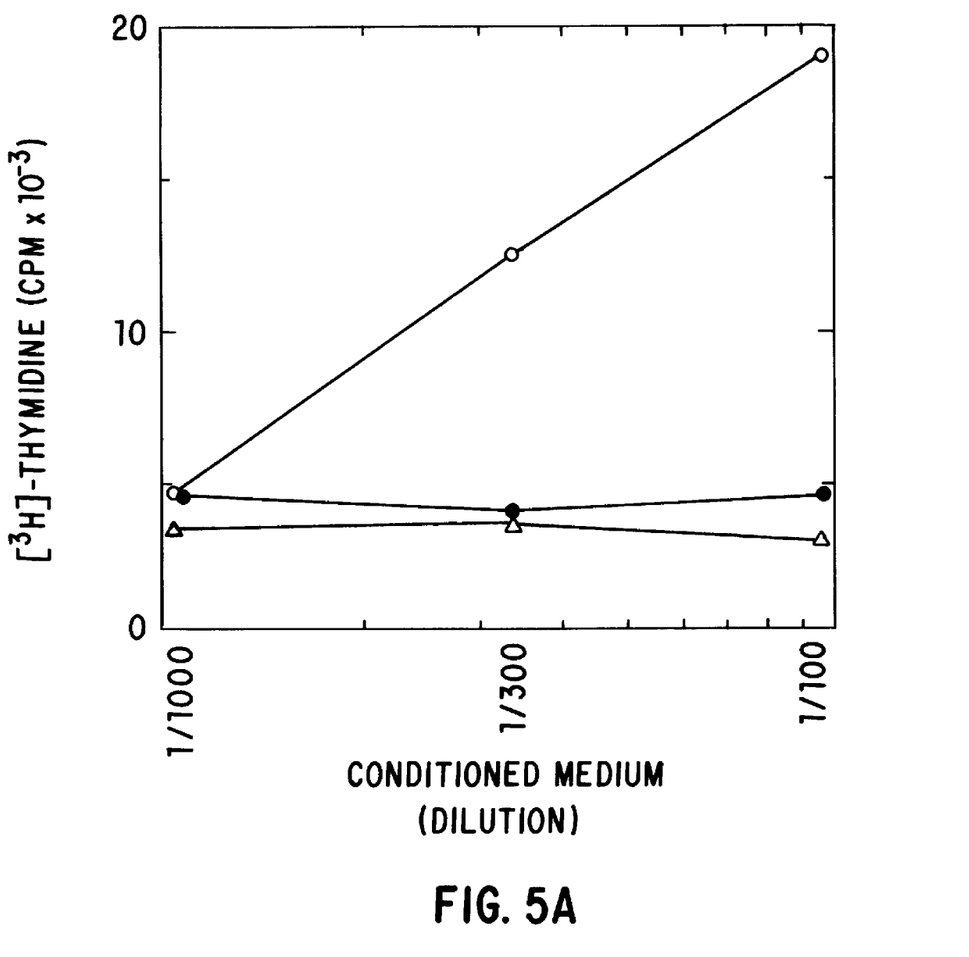
Figure 5B:
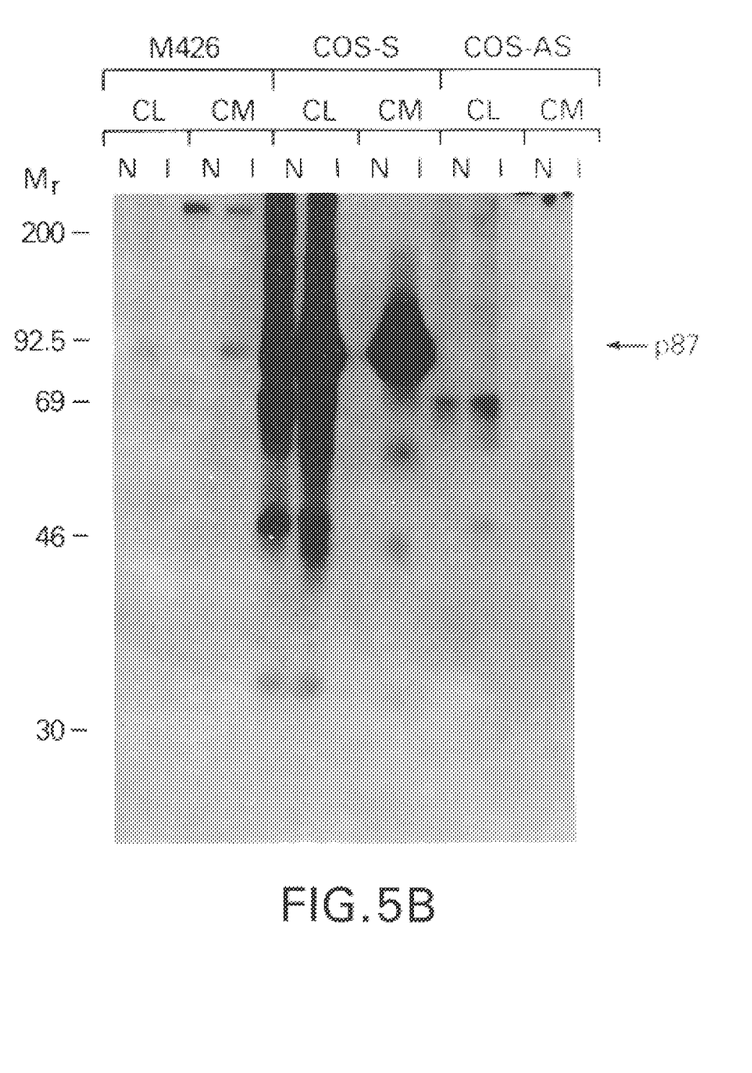
Figure 6A:
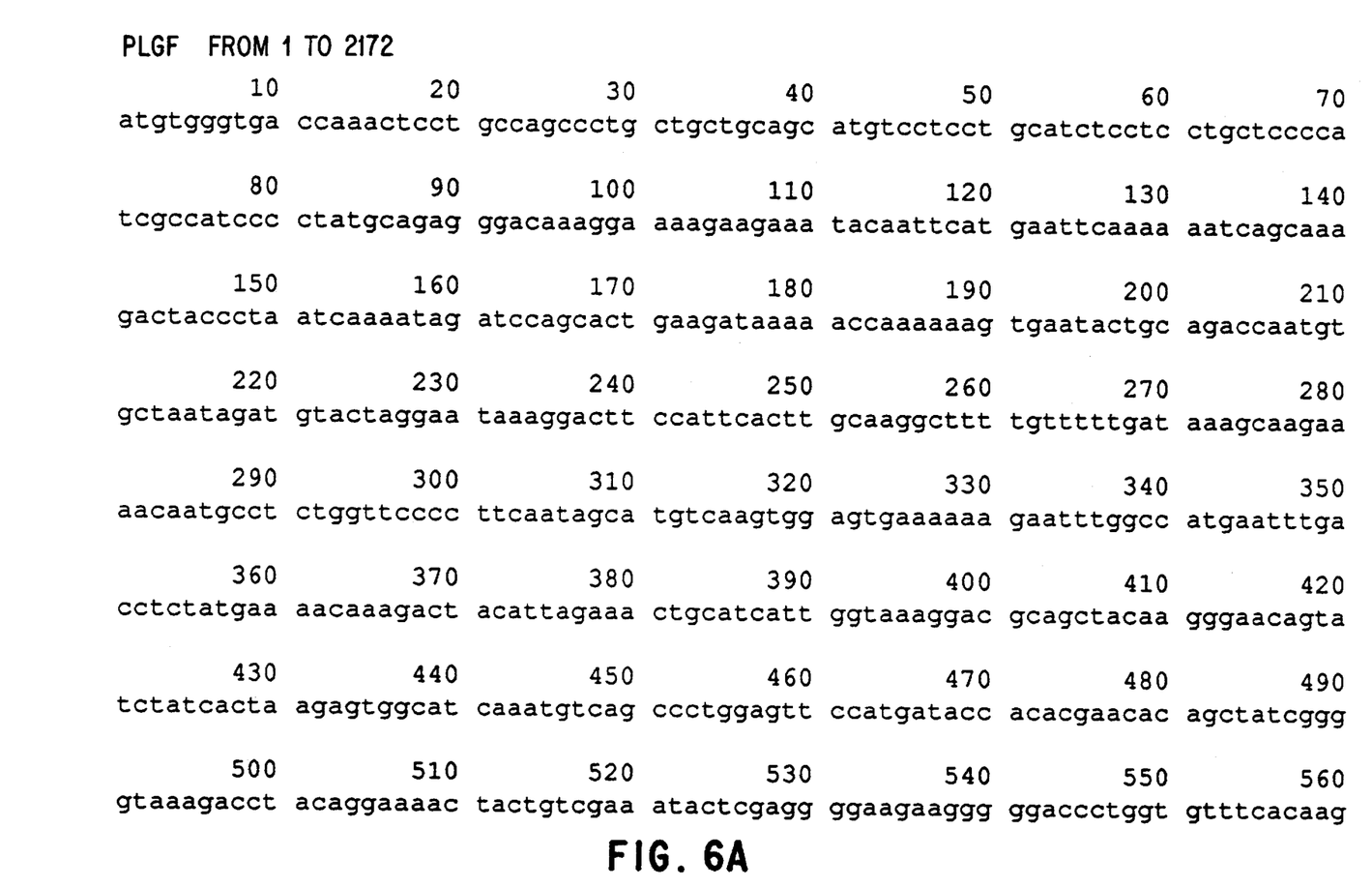
FIG. 6. The cDNA sequence of PLGF, having an open reading frame of 2172 nucleotides.
Figure 6B:
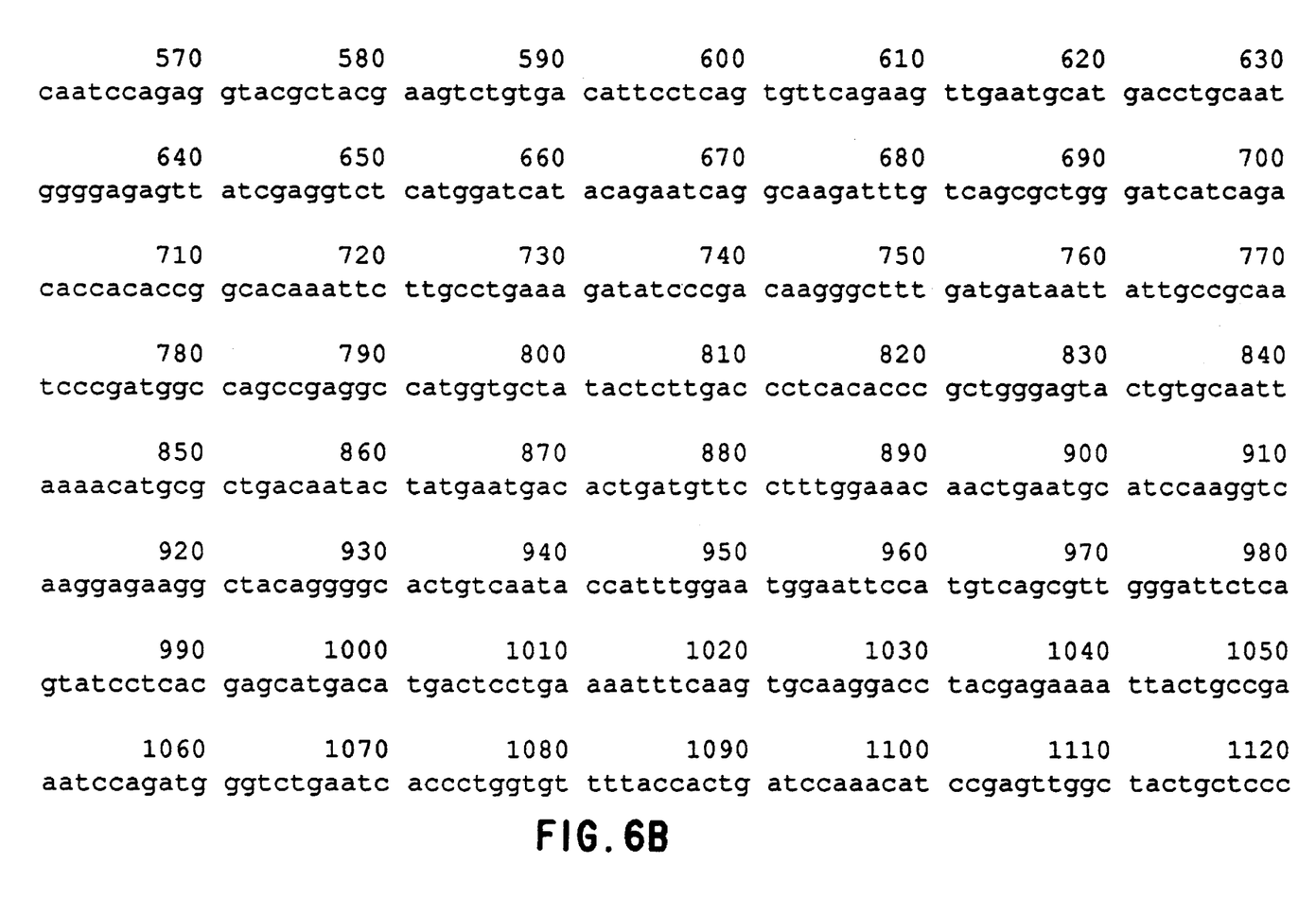
Figure 6C:
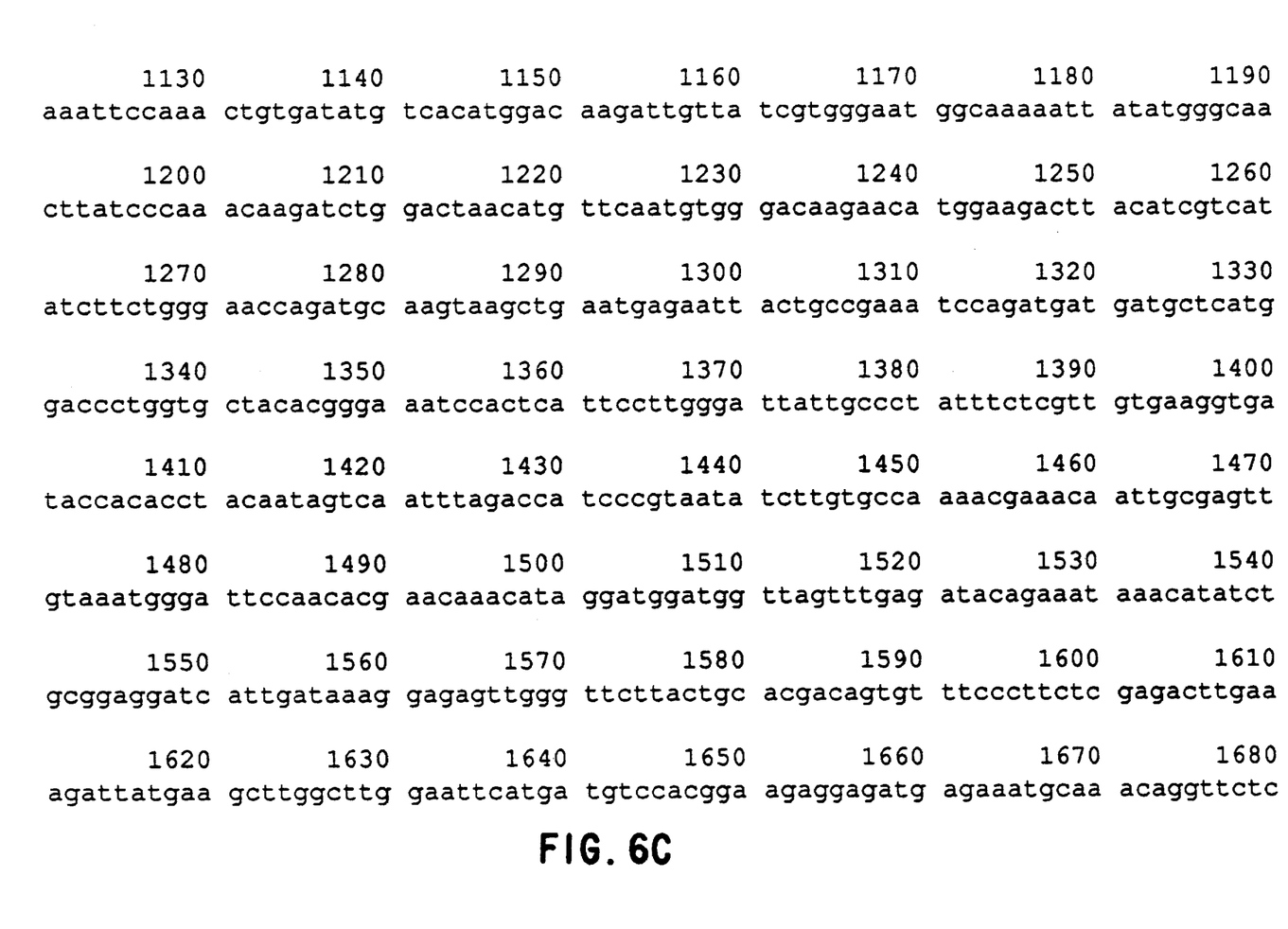
Figure 6D:
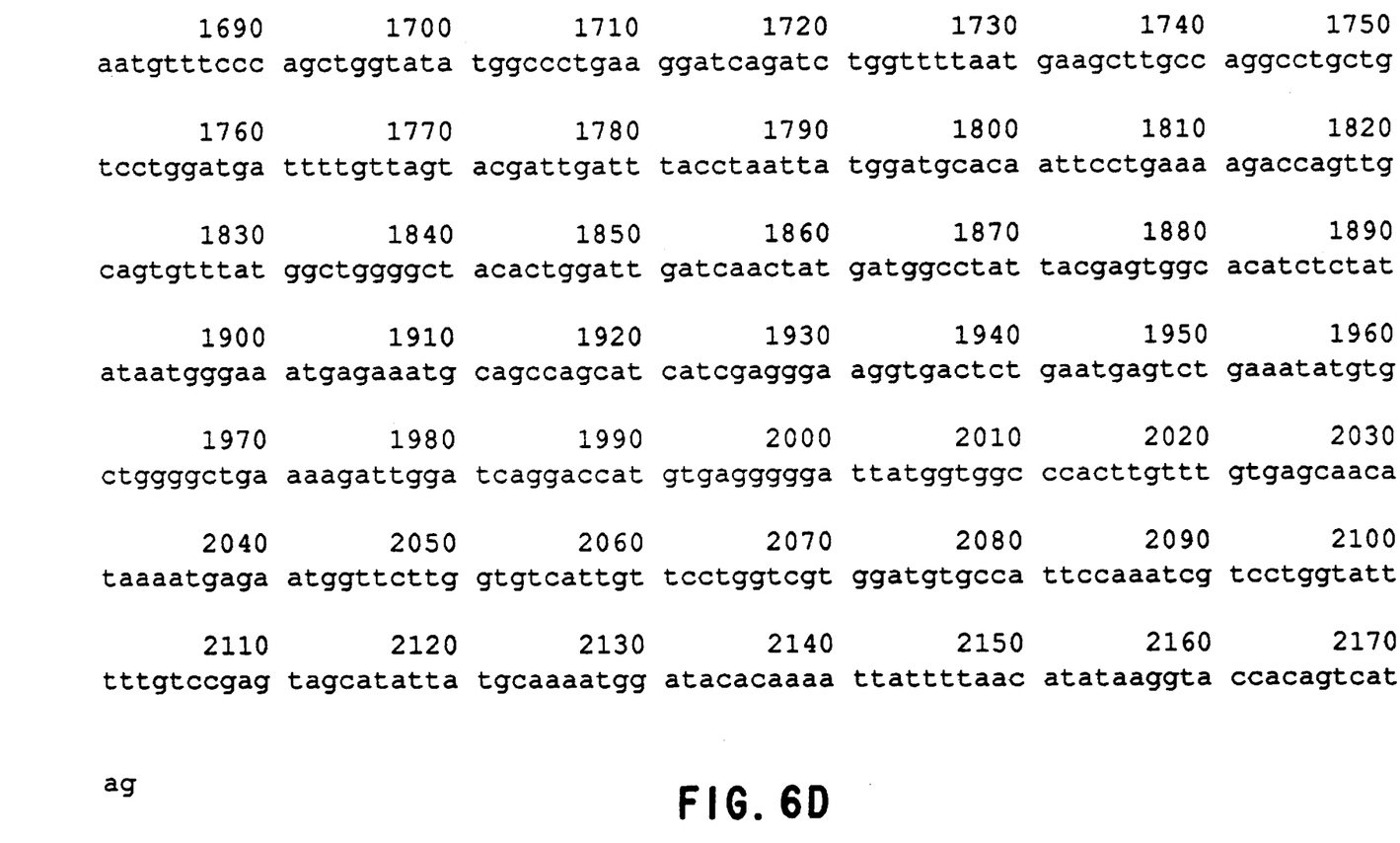

The present invention also relates to methods of diagnosing malignancy by detection of PLGF protein. In one such method, a biological sample from a patient is contacted with antibodies of the present invention specific for PLGF protein. Using standard methodologies well known in the art, the antibody-protein complex can be detected, for example by immunoprecipitation and SDS-polyacylamide gel electrophoresis as shown in FIG. 5B, as well as by immunoblot analysis, enzyme-linked immunosorbent assay (ELISA) or immunohistochemistry.

Figure 4B:
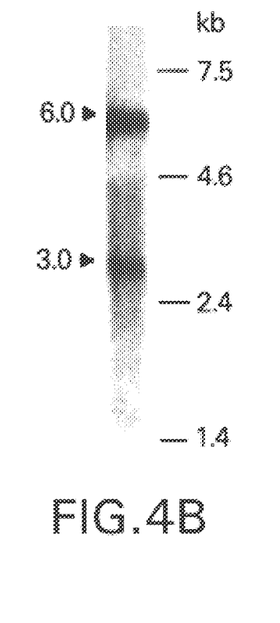

In another detection method for diagnosing malignancy the level of mRNA transcripts encoding the protein is detected. Increased levels of PLGF transcripts have been observed in selected malignant cell lines compared to other cells. Thus, by analyzing the level of MRNA expression, such disorders can be identified and characterized. As one skilled in the art will appreciate, increased protein production can result from increased levels of corresponding mRNA transcripts. Using DNA fragments encoding PLGF or portions thereof and standard methodology known in the art, PLGF transcripts can be identified, as shown in FIG. 4B. Detection may be performed with extracted RNA or by in situ hybridization.

The following non-limiting example illustrate the invention in more detail.

EXAMPLES

The following cell cultures and mitogenic assays were used throughout the Examples.

Cell Culture. The source and maintenance of the M426, BALB/MK, B5/589, CCL208 and NIH/3T3 cell lines were described previously (Rubin et al., (1989)). Primary cultures of human melanocytes (R. Halaban, In Vitro Cell. Dev. Biol. 23, 47–52 (1987) were prepared according to published techniques. Human umbilical vein endothelial cells (HUVEC), obtained from T. Maciag (Jerome H. Holland Laboratory for the Biomedical Sciences, Rockville, Md.), were established in the presence of 1 ng/ml recombinant acidic FGF (aFGF) and grown as described (T. Maciag et al., J. Cell. Biol. 91, 420–426, 1981) in medium 199, 10% (vol/vol) fetal calf serum (FCS), 1% penicillin-streptomycin, 1% L-glutamine and 5 units/ml heparin (bovine lung, Upjohn).

Mitogenic Assays. DNA synthesis in the B5/589, BALB/MK, CCL208 and NIH/3T3 lines (Rubin et al., 1989) as well as in primary melanocytes (Halaban, et al., 1987) was measured as described in these references. For proliferation assay (Maciag et al. (1981)), HUVEC were plated at a density of $4 \times 10^4$ cells/6 cm petri dish in basal medium (in the presence or absence of heparin) supplemented with recombinant aFGF or bFGF (10 ng/ml) or HSAC-purified, PLGF (~100 ng/ml). Medium was changed every 3 days. After 10 days, the cells were trypsinized and counted.

Microsequencing. Approximately 10 $\mu$g of $C_4$-purified growth factor was electrophoresed under reducing conditions in a 12.5% polyacrylamide-SDS mini-gell (Hoefer). After transfer to nitrocellulose (R. Friesel, W. H. Burgess, T. Maciag, Mol. Cell. Biol. 9, 1857–1865, 1989) p87 was incubated with 0.2 $\mu$g lysyl endopeptidase (1/20:enzyme/substrate, Boehringer-Mannheim) in 25 mM Tris/1 mM EDTA/5% acetonitrile/pH 8.5 at 37° for 18 hr. The reaction mixture was loaded onto a RP300 cartridge (2.1×30 mm) and resolved using a linear gradient of 0.1% trifluoracetic acid/acetonitrile (microbore LC, Applied Biosystems model 130). Purified peptide was subjected to several rounds of Edman degradation using a gas-phase protein sequenator (Applied Biosystems model 477), and phenylthiohydantoin-amino acid derivatives were identified with an automated on-line HPLC column (Applied Biosystems model 120A).

Molecular Cloning. Eight pools of 27-mer oligonucleotide probes were synthesized on the basis of the amino acid sequence Leu-Ala-Arg-Pro-Ala-Val-Leu-Asp-Asn determined by microsequencing of p87. All the probes contained four inosines at the degenerate third position of codons for Pro-Ala-Val-Leu to limit the redundancy to 64–256/pool. In addition, there are 45-mer oligonucleotide probes were synthesized to match different regions of the reported HGF sequence (Miyazawa et al., 1989): nucleotides (−74)–(−30), 1099–1143 and 2196–2240. The oligonucleotide pools and individual probes (50 pmol each) were 5'-end labeled with 83 pmol of [$\gamma$-$^{32}$P] ATP (3000 Ci/mmol, Amersham) and 10 units of T4 polynucleotide kinase. Recombinant phages from the M426 cDNA library (T. Miki et al., Gene 83, 137–146, 1989) were replica-plated onto nitrocellulose filters and hybridized for 18 hr at 42° in 6×standard saline citrate (SSC), 10×Denhardt's solution, 0.05% sodium pyrophosphate and sonicated salmon sperm DNA (250$\mu$g/ml). Filters hybridized with the degenerate pools were washed twice in 6×SSC, 0.1% SDS at room temperature and once at 54°, while those hybridized with the individual probes were washed twice in 2×SSC, 0.1% SDS at room temperature and once at 55°. Filters were air-dried and exposed to x-ray film at −70° C. with intensifying screens.

Recombinant Expression. A fragment of cDNA clone $\lambda$ [nucleotides (−27) to 2199] spanning the entire coding sequence was generated by use of the polymerase chain reaction (PCR) (Saiki et al., Science 230, 1350–1354, 1985) and subcloned into the BamH1 site of vector pCDV (Okayama, H. & Berg, P., Mol. Cell. Biol. 3, 280–289, (1983)) in either the sense or antisense orientation. Ten $\mu$g of each plasmid DNA was transfected by the calcium phosphate method (Sambrook, J. et al., Molecular Cloning: A Laboratory Manual (Cold Spring Harbor Press, N.Y.), 2nd ed., Vol. 3, pp. 16.1–16.8., (1989)) into ~$2 \times 10^5$ COS-1 cells (Gluzman et al., Cell 23, 175–82, 1981)) which had been maintained in Dulbecco's modified Eagle's medium (DMEM) supplemented with 10% FCS. Forty-eight hr after transfection, the medium was changed to 0.1% FCS in DMEM and conditioned medium harvested 16 hrs later. The medium was filtered and concentrated 25-fold in a Centricon-10 microconcentrator, and aliquots were diluted 100, 300 and 1000-fold for assay of mitogenic activity.

Biosynthetic Studies. COS-transfected cells (14 hr after switch to low serum-containing medium) and M426 cells grown in 10 cm petri dishes were incubated for 30 min in methionine-free medium [D Dulbecco Vogt modification of Eagle's MEM] supplemented with 50 μg/ml heparin (bovine lung, Sigma) which was then replaced with fresh medium containing [$^{35}$S]-methionine (1 mCi/5ml/dish). After 4 hr, the medium was collected and concentrated >10 fold in Centricon-10 microconcentrators. The cells were washed on ice once with 10 ml of PBS, lysed with 0.4 ml of buffer containing 10 mM Tris pH 7.4/150 mM NaCl/1 mM EDTA/10 mM KCl/1% NP-40/0.1% SDS/0.05% TWEEN 20, scraped off the dishes, and lysates were clarified by centrifugation (14,000×g, 30 min). Immunoprecipitations were performed with 10 μl of nonimmune or immune serum adsorbed to GammaBind-G agarose (Genex) and samples were analyzed by 10% NaDodSO$_4$-PAGE under reducing conditions.

Figure 1:
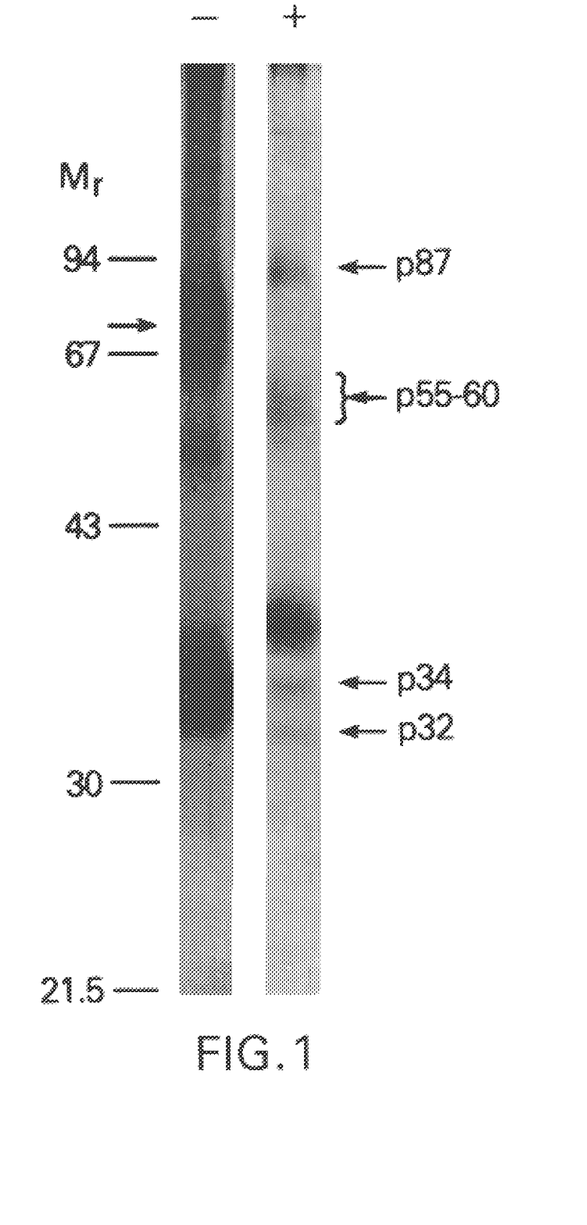

Example. Purification and Physical Characterization of a Fibroblast-Derived Mitogen contaminant 34 kD protein shifted to a higher apparent MW (FIG. 1). The pattern observed with the larger protein was more complex. A substantial portion migrated more slowly, consistent with loss of intrachain disulfide bonds. Moreover, additional bands with apparent MW of 55–60 kDa, 32 and 34 kD were observed with varying intensity in different preparations (FIG. 1). V8 proteolytic digestion and peptide mapping of individual bands from NaDodSO$_4$/PAGE supported the conclusion that p34 was a fragment of p87. These findings suggested that the broad, higher MW band present under nonreducing conditions was comprised of a mixture of polypeptides, including a single chain form (p87) and a processed, disulfide-linked heterodimer containing p55–60 and p32 or p34 chains.

Example 2. Unique Target Cell Specificity and Evidence of Mitogenic Signalling Involving Tyrosine Phosphorylation A summary of the responsive cells for this and other growth factors is provided in Table 1. Stimulation and detection of tyrosine phosphorylation was as described for KGF (Bottaro et al., 1990).

TABLE 1

Target-cell Specificity of Growth Factors
Fold Stimulation of [$^3$H] Thymidine Incorporation[1] or Cell Number[2]

| | Epithelial | | | Fibroblast | Endothelial | Melanocyte |
|---|---|---|---|---|---|---|
| Growth Factor | B5/589[3] | CCL208[4] | BALB/MK[5] | NIH/3T3 | HUVEC | Human Primary |
| PLGF | 10 | 10 | 40 | <1 | 3 | 180 |
| KGF | 3 | 10 | 800 | <1 | ND | <1 |
| aFGF[6] | 3 | 10 | 800 | 60 | 3 | 100 |
| bFGF | 3 | 5 | 200 | 60 | 3 | 100 |
| EGF | 15 | 20 | 200 | 15 | ND | <1 |
| TGFα | ND | ND | 300 | 15 | ND | |

[1]Comparison of maximal thymidine incorporation stimulated by the newly identified growth factor and other well characterized factors expressed as fold stimulation over background. Typical background levels were as follows: B5/589, 3000 cpm; CCL208, 1000 cpm; BALB/MK, 200 cpm; NIH/3T3, 3000 cpm; melanocytes, 500 cpm. These data are representative of several experiments.
[2]Results for endothelial cells were from proliferation assays.
[3]These cells also have been designated AB589.
[4]A rhesus monkey bronchial epithelial line.
[5]A mouse epidermal keratinocyte line.
[6]Maximal stimulation by aFGF required the presence of heparin.
ND Not determined PLGF with activity on mouse keratinocytes (BALB/MK) was isolated from conditioned medium of M426 human embryonic lung fibroblasts by a combination of ultrafiltration, heparin-Sepharose affinity chromatography (HSAC) and reverse-phase C$_4$ HPLC. The growth factor activity eluted from heparin-Sepharose with 0.8–0.9 NaCl, and from the C$_4$ resin with 0.1% TFA/~48% acetonitrile. Recovery of activity after C$_4$ HPLC required prompt dilution and neutralization or immediate drying of fractions in vacuo. The purification scheme routinely yielded 20–40 μg of protein from 8 liters of conditioned medium. Assuming no contribution from other mitogens or inhibitors in the medium, it is estimated that the purification resulted in an enrichment of ~1500 fold and yield of 5–10% activity.

Figure 2:
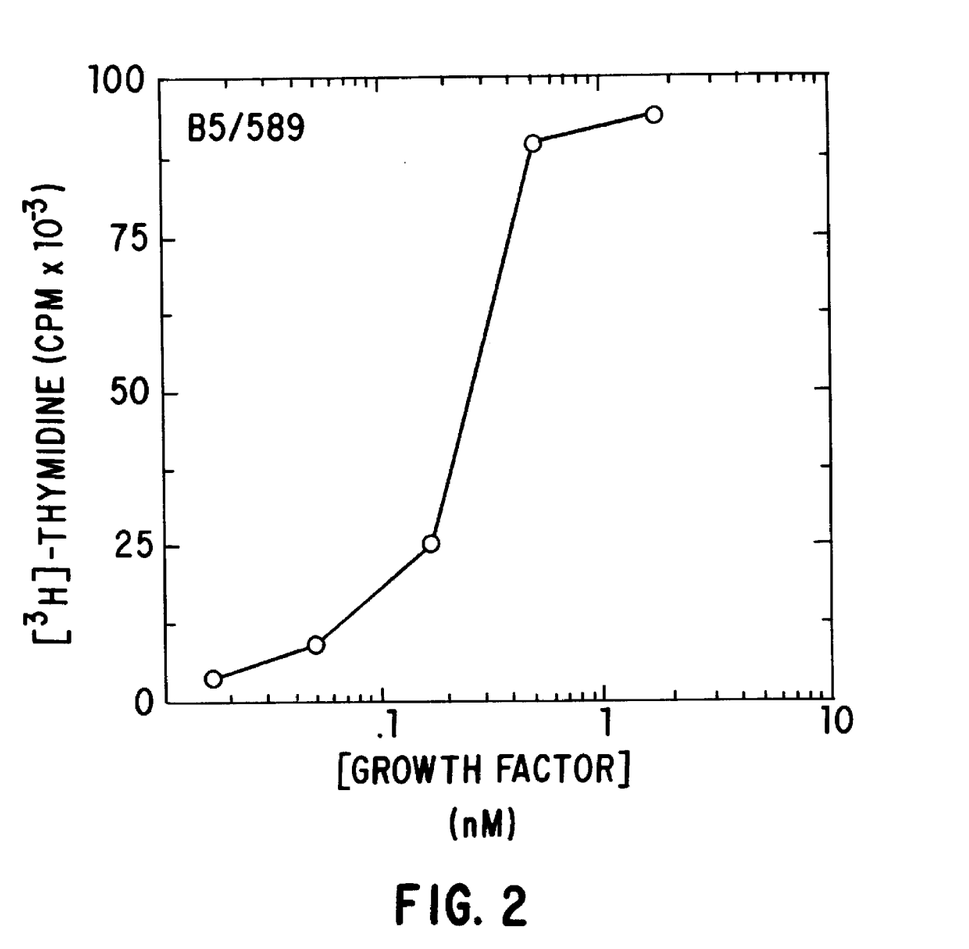

Analysis of the C$_4$-purified pool by NaDodSO$_4$/PAGE under non-reducing conditions revealed two broad bands at ~75 kD and ~34 kD (FIG. 1). NaDodSO$_4$/PAGE analysis of individual HSAC and C$_4$-HPLC fractions established that the intensity of the 75 kD but not the 34 kD band correlated with mitogenic activity. Under reducing conditions, the Significant stimulation was evident on mammary and bronchial epithelial cells as well as keratinocytes, while there was no detectable activity on fibroblasts. Of note, the factor elicited as strong a response as the FGFs on endothelial cells and was even more potent than the FGFs on human melanocytes (Table 1). Thus, the factor exhibited a broad target cell specificity, whose pattern was distinct from known growth factors. In contrast to the FGFs, whose activity on endothelial cells was enhanced or unaltered by heparin, proliferation in response to the new growth factor was markedly inhibited by heparin. A similar inhibitory effect of heparin was observed with other target cells. It is estimated that the half-maximal mitogenic effect of the C$_4$-purified factor, when expressed in terms of molarity (assuming MW 87 kD) was ~250 pM, well within the range of polypeptide growth factors (FIG. 2).

Figure 3:
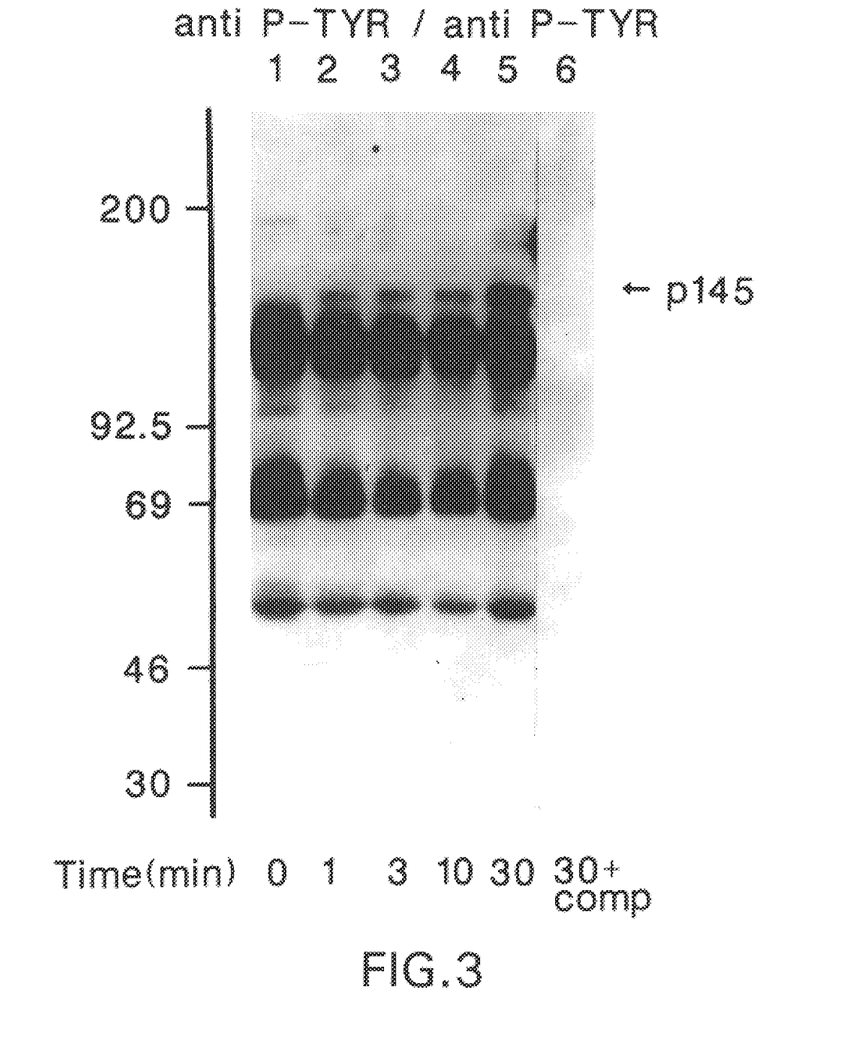

Because many growth factor receptors possess tyrosine kinase activity (Hunter, T. & Cooper, J. A. (1985) Annu. Rev. Biochem. 57, 443–478; Yarden, Y. & Ullrich, A. (1988) Annu. Rev. Biochem. 57, 443–478.), the possibility that PLGF triggered tyrosine phosphorylation in target cells was investigated. When B5/589 cells were exposed to the growth factor, a rapid appearance of a 145 kD tyrosine phosphorylated band was observed (pp145, FIG. 3). The band was specifically competed by an excess of phenyl phosphate, an analog of phosphotyrosine (FIG. 3). The intensity of the tyrosine phosphorylated pp145 decreased after 30–60 min but was still detectable 2 hrs following growth factor addition. All of these findings are consistent with the possibility that pp145 represents an autophosphorylated receptor with tyrosine kinase activity. In any case, the appearance of pp145 argues that PLGF growth factor rapidly activates tyrosine phosphorylation in its target cells.

Example 3. Molecular Identification and Cloning Reveals Homology to Hepatocyte Growth Factor To establish the identity of this broad spectrum mitogen, PLGF, amino acid sequence information was obtained. While p87 appeared to have a blocked amino terminus, digestion with lysyl endopeptidase yielded soluble peptides that were resolved by reverse-phase HPLC for sequence analysis. From one, positive identifications were made through the first nine cycles; the amino-terminal assignment was inferred from the cleavage specificity of lysyl endopeptidase: (Lys)-Leu-Ala-Arg-Pro-Ala-Val-Leu-Asp-Asn.

During efforts to isolate cDNA clones using degenerate oligonucleotide probes based upon this amino acid sequence, two reports appeared concerning the predicted protein sequence of hepatocyte growth factor (HGF) (Miyazawa, K. et al. (1989) Biochem. Biophys. Res. Comm. 163, 967–973; Nakamura, R. et al. (1989) Nature 342, 440–443.), which had been purified from human plasma (Gohda, E. et al., (1988) J. Clin. Invest. 81, 414–419) or rat platelets (Nakamura, T., et al. (1987) FEBS Lett 224, 311–316). The hepatocyte growth factor, also referred to as hepatopoietin A (Zarneger, R. & Michalopoulos, G. (1989) Cancer Res. 49, 3314–3320), acts on hepatocytes and is thought to be important for liver regeneration (Miyazawa, K. et al., (1989) Biochem. Biophys. Res. Comm. 163, 967–973, Nakamura, T. et al., (1989) Nature 342, 440–443; Zarnegar, R. & Michalopoulos, G. (1989) Cancer Res. 49, 3314–3320). The first nine amino acids of this protein sequence were identical to a region of the predicted HGF sequence. By use of oligonucleotide probes based upon the above amino acid sequence as well as those corresponding to three different regions of the HGF cDNA sequence, 35 positive clones out of an estimated 500,000 were identified and screened in the M426 cDNA library. One was large enough (~6 kb) to be almost full length according to the reported size of the HGF mRNA (Miyazawa, K. (1989) Biochem. Biophys. Res. Comm. 163, 967–973; Nakamura, T. et al., (1989) Nature 342, 440–443) and the results obtain in these studies (FIG. 4A and 4B). Several other ~3 kb clones were found by restriction mapping to match the 5' half of the largest insert (FIG. 4A). Northern blot analysis of M426 cellular RNA revealed in addition to a 6 kb transcript, a 3 kb transcript not reported previously for HGF (FIG. 4B). Thus, the 3 kb clones could have arisen from the 3 kb transcript or from the 6 kb mRNA by internal priming.

Figure 4C:
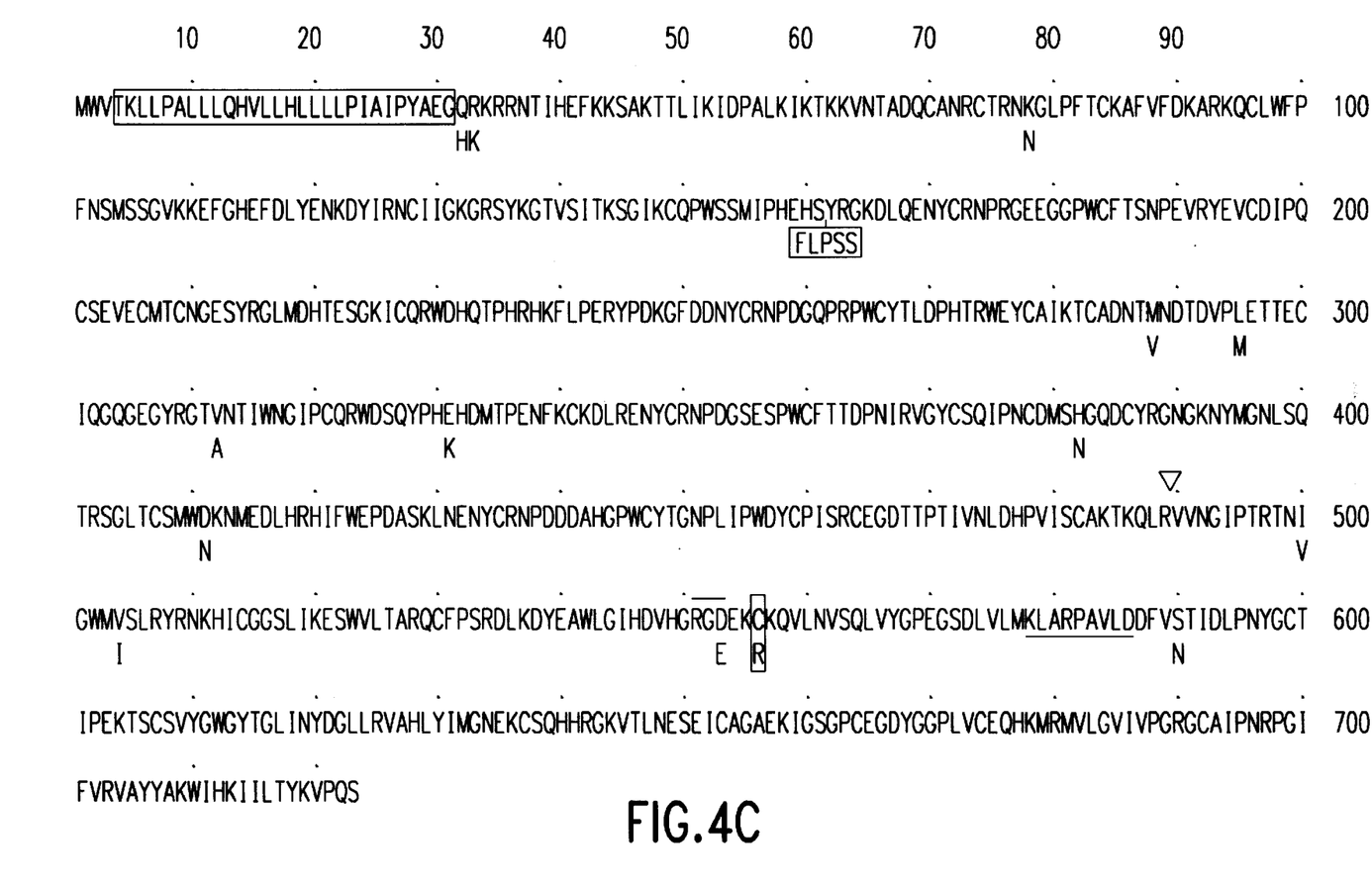

A representative 3 kb cDNA clone designated λ1a was sequenced by the dideoxy chain-termination method (Sanger et al., Proc. Natl. Acad. Sci. USA 74, 5463–5467, 1987) of overlapping fragments that had been subcloned into M13 vectors. Confirmatory data were obtained with clones λ9 and λ22. The DNA sequence was deposited at GenBank located in Los Alamos, NM on Oct. 6, 1990. The cDNA sequence may be requested from GenBank by accession number M55379. It contained an open reading frame of 2172 nucleotides predicting a protein with a MW of 82,606. There were four potential N-linked glycosylation sites (Asn residues 289, 397, 561 and 648) and a putative signal peptide sequence at the amino-terminus (FIG. 4C). Taking into account post-translational modifications, the predicted protein corresponded in size to p87. Comparison with the sequence of Miyazawa et al. for HGF (Miyazawa, K. et al., (1989) Biochem. Biophys. Res. Comm. 163, 967–973), revealed complete identity including four kringle structures and a protease-like domain, except for the absence of a 5 amino acid stretch caused by a 15 bp deletion (FIG. 4C). The sequence also differed from the HGF sequence of Nakamura et al. (Nakamura, T. et al., (1989) Nature 342, 440–443) in this region and showed 14 other single amino acid substitutions scattered throughout the molecule (FIG. 4C).

PCR analysis revealed that the 6 kb cDNA clone as well as about one half of the 3 kb cDNA clones exhibited the 15 bp deletion, while the other half did not. When PCR analysis was performed on RNA prepared from M426 fibroblasts as well as from the fibroblasts of 18 other individuals, both sequences in every instance were detected, arguing strongly that the different forms were due to alternative RNA splicing (Breitbart et al., Annu. Rev. Biochem. 56, 467–495, 1987).

Example 4. Preparation of Specific Neutralizing Antiserum to PLGF

The specific neutralizing antiserum was prepared by injecting 10 μg of $C_4$-purified PLGF growth factor into the inguinal lymph nodes of a rabbit, and boosting intranodally as well as intramuscularly with highly purified $C_4$ fractions containing μg quantities of the factor. An immunoglobulin G fraction was prepared with GammaBind-G agarose (Genex), according to the manufacturer's protocol. Nonimmune serum was an immunoglobulin G fraction from the same rabbit obtained prior to immunization.

Example 5. Recombinant CDNA Expression Confirms the Identity and Properties of the Mitogen To directly establish that the cloned sequence encoded the broad spectrum mitogen, the λ1a coding sequence was introduced into the PCDV expression vector and cell lysates and conditioned medium following transient expression in COS-1 cells were analyzed. As shown in FIG. 5A, medium from cells transfected in the 'sense' but not 'antisense' orientation caused potent stimulation of $^3$H-thymidine incorporation by B5/589 human mammary epithelial cells. The recombinant material exhibited the same broad target cell specificity and was neutralized by antiserum that efficiently blocked mitogenic activity of the naturally occurring growth factor (FIG. 5A). Metabolic labeling of M426 and transfected COS cells revealed that p87 was detected in cell lysates and was the predominant species secreted by the cells (FIG. 5B). Thus, the recombinant factor was synthesized and secreted as a single polypeptide chain. All of the above findings established that the molecular clone λ1a encoded the purified, broad spectrum mitogen.

Example 6. Relationship of PLGF to Malignancy

Ongoing studies have demonstrated a potential relationship of PLGF to malignancy. Transfection of PLGF into a non-tumorigenic target call, B5/589 confers the ability to grow in soft agar, an attribute of transformed cells. Moreover, certain transformed cell lines derived from malignant tumors express both PLGF and its receptor, raising the possibility that a positive autocrine loop contributes to the uncontrolled proliferation of these cells. Reagents such as the neutralizing antiserum against PLGF have been shown to reduce the rate of DNA synthesis by cells expressing both the growth factor and its receptor. It now appears that the PLGF receptor corresponds to the major tyrosine-phosphorylated band seen in response to PLGF (p145), and is itself a previously identified proto-oncogene with tyrosine kinase activity. Thus, there is reason to believe that PLGF may play a role in certain malignancies, and therefore its detection and inhibition could be of diagnostic or therapeutic significance in these disorders.

While the foregoing invention has been described in some detail for purposes of clarity and understanding, it will be appreciated by one skilled in the art from a reading of this disclosure that various changes in form and detail can be made without departing from the true scope of the invention and appended claims.

The entire contents of all references cited above are incorporated herein by reference.

What is claimed is:

1. A method of stimulating the growth of epithelial cells, comprising contacting cells with plasminogen-like growth factor protein (PLGF) substantially free of proteins with which it is normally associated, under conditions such that cell growth is stimulated, wherein said PLGF is encoded by DNA comprising the sequence in FIG. 6 or species, allelic or splice variants thereof and wherein said epithelial cells are selected from the group consisting of cells from the epidermis, mammary tissue, respiratory tract, gastrointestinal tract and prostate tissue.

2. The method of claim 1, wherein said epidermis cells are either melanocytes or keratinocytes.

3. The method of claim 1, wherein said PLGF comprises the amino acid sequence of FIG. 4C.

4. A method of stimulating wound healing in epithelial tissue, said method comprising contacting said tissue with a wound healing effective amount of plasminogen-like growth factor protein (PLGF) and a pharmaceutically acceptable carrier, wherein said PLGF is encoded by DNA comprising the sequence in FIG. 6 or species, allelic or splice variants thereof and wherein said epithelial tissue is selected from the group consisting of tissue from the epidermis, mammary tissue, respiratory tract, gastrointestinal tract and prostate tissue.

5. A method of stimulating the growth of epithelial cells, comprising contacting cells with plasminogen-like growth factor protein (PLGF) substantially free of proteins with which it is normally associated, under conditions such that cell growth is stimulated, wherein said PLGF is encoded by DNA comprising the sequence of FIG. 6 or species, allelic or splice variations thereof and wherein said epithelial cells are not hepatocytes.

6. A method of stimulating wound healing in epithelial tissue, said method comprising contacting said tissue with a wound healing effective amount of plasminogen-like growth factor protein (PLGF) and a pharmaceutically acceptable carrier, wherein said PLGF is encoded by DNA comprising the sequence of FIG. 6 or species, allelic or splice variations thereof and wherein said epithelial tissue is not hepatocyte tissue.

7. The method of claim 5 or 6, wherein said PLGF comprises the amino acid sequence of FIG. 4C.

8. A method of stimulating the growth of endothelial cells, comprising contacting cells with plasminogen-like growth factor protein (PLGF) substantially free of proteins with which it is normally associated, under conditions such that cell growth is stimulated, wherein said PLGF is encoded by DNA comprising the sequence in FIG. 6 or species, allelic or splice variations thereof.

9. The method of claim 8, wherein said cell growth promotes angiogenesis.

10. A method of stimulating wound healing in endothelial tissue, said method comprising contacting said tissue with a wound healing effective amount of plasminogen-like growth factor protein (PLGF) and a pharmaceutically acceptable carrier, wherein said PLGF is encoded by DNA comprising the sequence in FIG. 6 or species, allelic or splice variations thereof.

* * * * *